United States Patent [19]

Orban et al.

[11] 4,275,211
[45] Jun. 23, 1981

[54] PROCESS FOR PREPARING 2,2,6,6-TETRAALKYL-4-OXOPIPERIDINES

[75] Inventors: Ivan Orban; Eduard Troxler, both of Basel, Switzerland

[73] Assignee: Ciba-Geigy Corporation, Ardsley, N.Y.

[21] Appl. No.: 91,006

[22] Filed: Nov. 5, 1979

[30] Foreign Application Priority Data

Nov. 17, 1978 [CH] Switzerland ............... 11829/78

[51] Int. Cl.³ .................................... C07D 211/74
[52] U.S. Cl. .................................... 546/242
[58] Field of Search ......................... 546/242

[56] References Cited

U.S. PATENT DOCUMENTS

| | | | |
|---|---|---|---|
| 3,513,170 | 5/1970 | Murayama et al. | 546/242 |
| 3,904,625 | 9/1975 | Alink | 544/231 |
| 3,953,459 | 4/1976 | Orban et al. | 546/242 |
| 3,959,295 | 5/1976 | Orban et al. | 546/242 |
| 3,963,730 | 6/1976 | Murayama et al. | 546/242 |

FOREIGN PATENT DOCUMENTS 2807172  8/1979  Fed. Rep. of Germany .......... 546/242

OTHER PUBLICATIONS

Astle, M. In Ion Exchangers in Organic and Biochemistry, Calmon et al., (Editors), Interscience, NY, 1957, pp. 662–665.

*Primary Examiner*—Richard A. Schwartz
*Attorney, Agent, or Firm*—Harry Falber

[57] ABSTRACT

A process for producing piperidines of the formula (I)

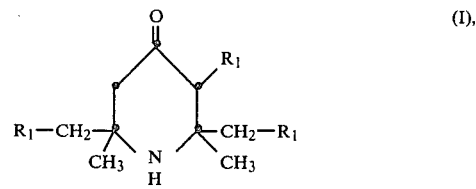

in which $R_1$ is hydrogen or $C_1$–$C_4$-alkyl, from a ketone of the formula (II) $R_1$—$CH_2$—$C(O)$—$CH_3$, wherein $R_1$ has the meaning given above, and ammonia, in which process there is used as catalyst a strongly acid ion exchanger having a medium or large mesh size or having large macropores.

8 Claims, No Drawings

PROCESS FOR PREPARING 2,2,6,6-TETRAALKYL-4-OXOPIPERIDINES

The present invention relates to a new process for producing 2,2,6,6-tetraalkyl-4-oxopiperidines.

Various processes for producing 2,2,6,6-tetraalkyl-4-oxopiperidines, which have gained importance especially as intermediates for producing light stabilisers, are known. Thus, for example, there is described in the U.S. Pat. No. 3,959,295 a process which yields 2,2,6,6-tetramethyl-4-oxopiperidine starting with acetone and ammonia, in the presence of an acid catalyst. Attempts to find a process catalysed by ion exchange have however hitherto met with no success.

The advantages which a process catalysed by ion exchange would offer, for example economy in operation by virtue of repeated utilisation, negligible pollution of the environment and easy separation of the final product, as well as good storage stability of the products since they are not contaminated with soluble catalyst, and so forth, are familiar to one skilled in the art.

Efforts made hitherto to react acetone and ammonia by ion exchange catalysis yielded however merely 2,2,4,4,6-pentamethyl-2,3,4,5-tetrahydropyrimidine. Such processes with acid and basic ion exchangers as catalysts are described for example in the U.S. Pat. No. 3,904,625.

It has now been found that, surprisingly, ion-exchange catalysed reactions between ketones and ammonia readily yield 2,2,6,6-tetraalkyl-4-oxopiperidines in the case where strongly acid ion exchangers having a specific matrix structure are used.

The present invention relates to a process for producing piperidines of the formula (I)

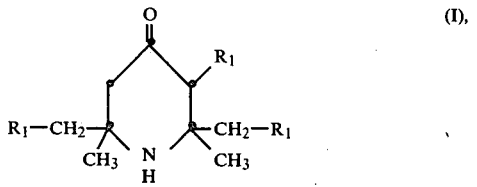

in which $R_1$ is hydrogen or $C_1$-$C_4$-alkyl, from a ketone of the formula (II) $R_1$—$CH_2$—$C(O)$—$CH_3$, wherein $R_1$ has the meaning given above, and ammonia, in which process there is used as catalyst a strongly acid ion exchanger having a medium or large mesh size or having large macropores.

In the formulae (I) and (II), $R_1$ as $C_1$-$C_4$-alkyl is for example n-butyl, t-butyl, n-propyl, ethyl or preferably methyl. In particular however $R_1$ is hydrogen.

Strongly acid cation exchangers are produced mainly based on styrene, with the crosslinking agent used being for example divinylbenzene. These copolymers are sulfonated with the customary sulfonating agents. In order to obtain the structure of the ion exchanger matrix fundamental for the present invention, there are essentially two methods which can be applied:

(a) When on copolymerisation of styrene and divinylbenzene (DVB) the proportions of DVB are kept low, copolymers of medium or low crosslinkage are obtained, that is to say, the meshes of the three-dimensional network are medium or large in size. Meshes designated as being of medium or large size are those having an average width of 10–20 Å. Copolymers preferred for the present invention are those having large mesh sizes, that is, a mesh size of 12–20 Å. Resins of this kind have become known under the name of gel resins.

(b) When on copolymerisation of styrene and DVB, there are concomitantly used inert materials, with these being removed, for example by evaporation or elution, after polymerisation has been performed, so-called macroporous resins are obtained. The best results for the present reaction are obtained with large pores, of which the mean pore diameter is above about 500 Å, preferably above 600 Å. Although this minimum mean pore diameter constitutes a substantial feature of the invention, the use of resins having larger pores is always possible. Thus, at the present time ion exchangers having mean pore diameters of 1300 Å and larger are obtainable commercially. Ion exchangers having pore diameters of about 500–800 Å are particularly common.

The reaction of ammonia with the ketones of the formula II is performed in a manner known per se, for example by passing ammonia into the ketone, in the presence of the catalyst, at temperatures of 5° to 90° C., preferably at 40° to 75° C. The reaction can be carried out batchwise, and, using a variant which is especially preferred for ion exchangers, also continuously, with for example the ketone and ammonia being brought into contact in a column filled with the catalyst to be used according to the invention, in which process the excess ketone can be continuously recycled. The essential advantages of the continuous mode of operation are the better space-time yield, increased operational safety as a result of a considerable reduction of the amount of acetone in the plant, and also a lower working intensity (for example in the processing of the ketone, and so forth). In the reaction catalysed according to the invention, the amount of by-products formed is particularly small. The molar ratio of ketone to ammonia in this reaction is at least 2:1, preferably 4:1. The ketone excess can however quite well be up to 50:1. It has been shown that the flow rate has virtually no effect on the conversion rate.

The reaction can be performed also under slightly elevated pressure (for example up to 1 bar excess pressure), a condition which in any case obtains at temperatures above the boiling point of the employed ketone. In batch working, the excess pressure can be up to 30 bars, preferably up to 5 bars.

Suitable ketones of the formula II are for example n-butyl methyl ketone, n-propyl methyl ketone, preferably ethyl methyl ketone, and particularly acetone. It is furthermore possible to use condensation products of these ketones with themselves or with ammonia. This is of importance particularly in the case of acetone. Thus acetone can be replaced, completely or partially, by an acid condensation product with itself, such as diacetone alcohol, mesityl oxide or phorone, and also by an acid condensation product of acetone with ammonia, such as diacetonamine, triacetone diamine or acetonine. If acetonine is used in place of acetone, it is possible to dispense with ammonia either completely or partially since acetonine already intramolecularly contains the ammonia to be used according to the invention. It is of course also possible to use mixtures of several condensation products.

The alkylated 4-oxopiperidines produced according to the invention are isolated in a manner known per se, for example by crystallisation and filtration of the piperidine hydrate; or by distillation of the product. The last-mentioned distillation variant can likewise be performed continuously.

EXAMPLE 1

138 g (2.38 mols) of acetone and 5.8 g (0.34 mol) of ammonia are passed per hour through a reaction vessel, 83 cm in height and 6.5 cm in diameter, filled with an acid ion exchanger Lewatit SPC 118 H ®, freed from water, (total 1018 g) in 480 g of acetone. The first contact point is situated in the upper 13 cm long part which has an internal temperature of 25° to 40° C. The lower 70 cm long part is held at a temperature of 55° to 56° C. The consumed acetone (about 69 g/h) is continuously replaced, and the excess acetone is distilled off and is suppled afresh to the column by means of a condenser. The formed triacetonamine is continuously distilled and yields a distillate of 30.9 g/h.

It is also possible to isolate the formed 2,2,6,6-tetramethyl-4-oxopiperidine (triacetonamine), instead of by distillation, for example as hydrate by crystallisation.

EXAMPLE 2

Practically the same results as in Example 1 are obtained by using Lewatit SC 102/H ® as the catalyst, with otherwise the same procedure as in Example 1.

EXAMPLE 3

When Lewatit SC 104/H ® is used as the catalyst, the procedure otherwise being as in Example 1, there is readily formed triacetonamine with only slightly reduced yield.

EXAMPLE 4

Approximately the same amounts of triacetonamine as in Example 1 are obtained by using, in place of 138 g of acetone per hour, a ketone mixture consisting of 87 g (1.5 mols) of acetone, 30 g (0.3 mol) of mesityl oxide and 17 g (0.14 mol) of diacetone alcohol, the procedure otherwise remaining the same as in Example 1.

EXAMPLE 5

Triacetonamine is obtained in yields identical to those in Example 1 by using, instead of 138 g of acetone per hour, a solution of 23 g (0.15 mol) of acetonine hydrate, 107 g (1.84 mols) of acetone and 8 g (0.44 mol) of water, the procedure otherwise being the same as in Example 1.

EXAMPLE 6

The reaction described in Example 1 is performed with flow rates of 12 cm/h/cm² and 500 cm/h/cm², respectively. The two tests yield after the same test time virtually identical conversions.

EXAMPLE 7

If the procedure is carried out as described in Example 1 except that the catalyst used is Amberlist 15 ®, there is obtained triacetonamine in a yield identical to that in Example 1.

EXAMPLE 8

If the procedure is carried out as described in Example 1 except that the catalyst used is Amberlite 200 ®, there is obtained triacetonamine in a yield identical to that in Example 1.

EXAMPLE 9

The test arrangement described in Example 1 is varied as follows: Acetone and ammonia are introduced, in the amounts given in Example 1, into a reaction vessel from below. The temperature in the lowest part of the reaction vessel is 20°-65° C., and in the upper longer part it is 65° C. Triacetonamine is formed in the process in an amount practically the same as that in Example 1.

EXAMPLE 10

When the catalyst in Example 1 is replaced by Duolite ® (organic ion exchanger, weakly acid, macroporous), by Amberlite IRC-50 ® (organic ion exchanger, weakly acid, gel), by Amberlite IR-4B ® (organic ion exchanger, weakly basic, gel), or by Amberlite IRA-900 ® (organic ion exchanger, strongly basic, macroporous), virtually no triacetonamine is obtained. The reaction of acetone and ammonia yields merely 2,2,4,4,6-pentamethyl-2,3,4,5-tetrahydropyrimidine.

What is claimed is:

1. In the process for producing a piperidine compound of the formula (I)

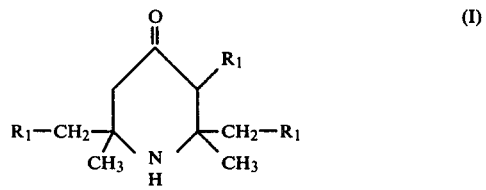

in which $R_1$ is hydrogen or $C_1$-$C_4$-alkyl, from a ketone of the formula (II) $R_1$—$CH_2$—$C(O)$—$CH_3$ (II), wherein $R_1$ has the meaning given above, and ammonia, at temperatures of 5°-90° C. in the presence of a catalyst, the improvement which comprises using as said catalyst a strongly acid ion exchanger having a medium or large mesh size, or having large macropores.

2. A process according to claim 1, wherein $R_1$ is hydrogen or methyl in the formulae (I) and (II).

3. A process according to claim 1, wherein $R_1$ is hydrogen in the formulae (I) and (II).

4. A process according to claim 3, wherein the ketone of the formula $CH_3$—$C(O)$—$CH_3$ (acetone) is replaced, either completely or partially, by diacetone alcohol and/or mesityl oxide, phorone, diacetonamine, triacetone diamine or acetonine.

5. A process according to claim 4, wherein the acetone is replaced by acetonine, and, since the ammonia to be used according to the invention is contained in the acetonine, any further addition of ammonia is dispensed with.

6. A process according to claim 1, wherein a gel resin having a mesh size of 10 to 20 Å is used.

7. A process according to claim 1, wherein a macroporous resin having a pore diameter of at least 500 Å is used.

8. A process according to claim 1, wherein a continuous mode of operation is chosen.

* * * * *